United States Patent
Altman

(10) Patent No.: US 6,577,895 B1
(45) Date of Patent: Jun. 10, 2003

(54) PULMONARY VEIN ARRHYTHMIA DIAGNOSTIC DEVICE AND METHOD FOR USE

(75) Inventor: Peter A. Altman, South San Francisco, CA (US)

(73) Assignee: BioCardia, Inc., So. San Francisco, CA (US)

( * ) Notice: Subject to any disclaimer, the term of this patent is extended or adjusted under 35 U.S.C. 154(b) by 58 days.

(21) Appl. No.: 09/687,884

(22) Filed: Oct. 13, 2000

Related U.S. Application Data

(60) Provisional application No. 60/159,343, filed on Oct. 13, 1999.

(51) Int. Cl.[7] .................. A61B 5/0402; A61M 25/10
(52) U.S. Cl. ........................ 600/518; 604/103.01
(58) Field of Search ................. 600/508, 509, 600/515, 518; 604/96.01, 103.01

(56) References Cited

U.S. PATENT DOCUMENTS

| | | | |
|---|---|---|---|
| 5,527,344 A | 6/1996 | Arzbaecher et al. | 607/3 |
| 5,899,917 A | 5/1999 | Edwards et al. | 606/195 |
| 6,012,457 A | 1/2000 | Lesh | 128/898 |
| 6,024,740 A | 2/2000 | Lesh et al. | 606/34 |
| 6,117,101 A | 9/2000 | Diedrich et al. | 604/22 |

FOREIGN PATENT DOCUMENTS

| WO | WO 99/52423 | 10/1999 |
|---|---|---|
| WO | WO 00/16850 | 3/2000 |
| WO | WO 00/42934 | 6/2000 |

*Primary Examiner*—Andrew M. Dolinar
(74) *Attorney, Agent, or Firm*—K. David Crockett; Crockett & Crockett

(57) ABSTRACT

Devices and methods for testing a pulmonary vein to determine whether or not ablation would be effective in terminating atrial fibrillation. The devices and methods include a catheter having an expandable balloon attached to the distal end of the catheter. The balloon has pores on the distal end of the balloon for administering a fluid into the target pulmonary vein. The fluid inhibits the electrical impulses generated by the target pulmonary vein. Once the electrical impulses of the target pulmonary vein have been inhibited it can be determined whether or not the atrial fibrillation continues to occur. If the atrial fibrillation has been eliminated, then ablation or other therapy is appropriate. Thus, the devices and methods limit unnecessary treatment of a pulmonary vein.

11 Claims, 3 Drawing Sheets

PULMONARY VEIN ARRHYTHMIA DIAGNOSTIC DEVICE AND METHOD FOR USE

RELATED PATENT APPLICATION

This patent application claims priority to U.S. provisional patent application No. 60/159,343, filed Oct. 13, 1999.

FIELD OF THE INVENTIONS

The inventions described below relate to the field of diagnostic medical devices. Specifically the inventions relate to a device and method for diagnosing whether ablation of a portion of the pulmonary vein will eliminate atrial fibrillation originating in the pulmonary vein.

BACKGROUND OF THE INVENTIONS

Atrial fibrillation (AF) is a form of heart disease that afflicts millions of people. It is a condition in which the normal contraction of the heart is interrupted, primarily by abnormal and uncontrolled action of the atria of the heart. The heart has four chambers: the right atrium, right ventricle, the left ventricle, the left atrium. The right atrium pumps de-oxygenated blood from the vena cava to the right ventricle, which pumps the blood to the lungs, necessary for return flow of de-oxygenated blood from the body. The right atrium contracts to squeeze blood into the right ventricle, and expands to suck blood from the vena cava. The left atrium pumps oxygenated blood from the pulmonary veins (returning from the lungs), necessary for flow of oxygenated blood from the lungs. The left atrium contracts to squeeze blood into the left ventricle, which then pumps the blood into the aorta and thence to the entire body, and expands to suck blood from the pulmonary veins. The contractions of the atria normally occur in a controlled sequence with the contractions of the other chambers of the heart. When the left atrium or the right atrium fails to contract, contracts out of sequence, or contracts ineffectively, blood flow within the heart is disrupted. The disruption of the normal rhythm of contraction is referred to as an arrhythmia. The arrhythmia, known as atrial fibrillation, can cause weakness of the heart due to reduced ventricular filling and reduced cardiac output. Stroke due to clot formation in a poorly contracting atria (which may lead to brain damage and death), and even other life threatening ventricular arrhythmias can also occur.

There is a broad spectrum of situations which fall under the broad heading of AF. For example, in older patients where there is substantial heterogeneity in the conduction within the atrial tissue, the patient is said to have the tissue substrate for AF such that any trigger will result in maintaining AF. In younger patients, the tissue may have more homogeneous conduction and be less likely to have sustained AF. In the younger patient it may be the often reoccurrence of a premature depolarizing tissue which acts as a trigger that causes the clinical manifestation of problematic episodes of AF. Clearly, there is a continuous spectrum of degrees of triggered AF and conduction heterogeneity which acts as a substrate for this arrhythmia, and it is appropriate that a number of medical therapies are being developed to treat and diagnose this disease.

Atrial fibrillation can be treated by atrial ablation. There are two general approaches for providing ablative therapy to the heart for the treatment of atrial fibrillation. These shall be called the long linear ablative lesion approach, and the focal ablation approach.

In the long linear lesion approach, the heart tissue is killed along a linear pathway. The cardiac electrophysiologist does this to segment the heart into regions which are too small to sustain atrial fibrillation. Such an approach is very similar to performing the Maze procedure using radiofrequency, microwave, and ultrasound ablative energy sources on the end of catheters. In the Maze procedure, a number of incisions are made with a scalpel in an attempt to terminate inappropriate accessory pathways.

In the focal ablation approach, the heart tissue is killed at a single site. The cardiac electrophysiologist attempts to ablate the region of the heart that prematurely depolarizes, and which has been described as acting as a trigger for the initiation of atrial fibrillation. Recently, ablation of the junction of the pulmonary veins and the left atrium has been performed. Such ablations remove the possibility of triggers for AF initiating within the pulmonary veins, or at the region near the junction of the veins with the left atrial tissue. Such ablations may also remove disturbances introduced into the conduction pathway by the heterogeneity of the junction region anatomy.

SUMMARY

Focal ablation of the region within or adjacent to the pulmonary vein to terminate atrial fibrillation with different energy transfer techniques such as RF ablation, laser ablation, ultrasound ablation, cryoablation, and microwave ablation causes damage to the tissue which may affect the viability of the tissue. While the ablation reliably eliminates the source of atrial fibrillation, the concomitant damage to the pulmonary vein may give rise to side effects such as stenosis of the treated pulmonary vein. Confirming that ablation of a target pulmonary vein would produce the desired result of stopping the atrial fibrillation would therefore be a highly beneficial procedure. The devices and methods describe below allow testing of the pulmonary veins to determine whether or not ablation would be effective in terminating atrial fibrillation. The devices and methods include a catheter having an expandable balloon attached to the distal end of the catheter. The balloon has pores on the distal end of the balloon for administering a fluid into the target pulmonary vein. The fluid inhibits the electrical impulses in the target pulmonary vein. Once the electrical impulses of the target pulmonary vein have been inhibited then it can be determined whether or not the atrial fibrillation has ceased occurring. If the atrial fibrillation has been eliminated, then ablation or other therapy is appropriate. Thus, the devices and methods described herein limit unnecessary treatment of a pulmonary vein.

DETAILED DESCRIPTION OF THE INVENTIONS

Figure 1:
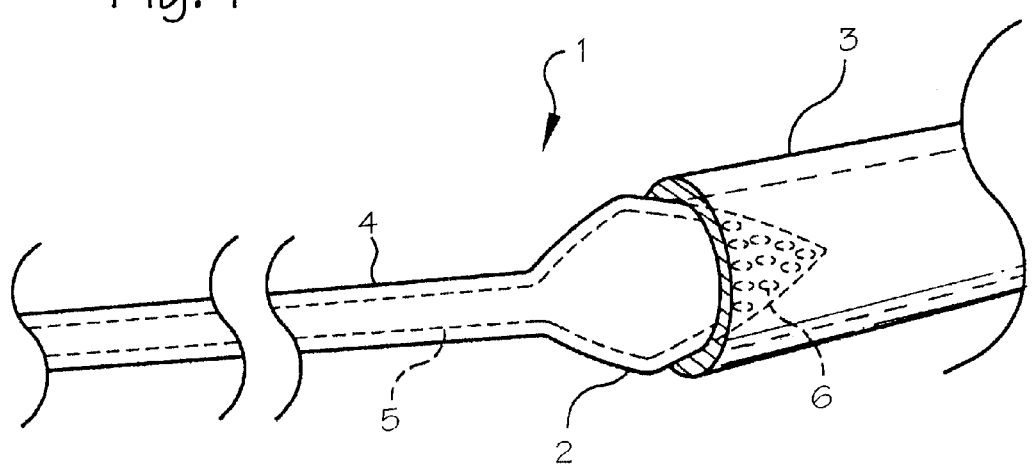
FIG. 1 is illustrates the diagnostic catheter designed for use in the pulmonary vein.

FIG. 1 shows the preferred embodiment of the diagnostic catheter 1 with the balloon 2 in its inflated state within the pulmonary vein 3. The catheter body 4 includes a fluid supply lumen 5 which extends from the proximal end of the catheter to the balloon, providing a fluid pathway from a fluid reservoir (not shown) at the proximal end of the catheter to the balloon.

The diagnostic catheter includes a catheter having a balloon 2 located at the distal end of the catheter. The balloon is adapted to contact the pulmonary vein 3 when the balloon is inflated. The balloon is provided in a conical or frustoconical shape, allowing it to seat against the flared shape of the ostium 14 (the ostium is the junction between the pulmonary vein and the atrium) with the tip of the cone penetrating into the pulmonary vein and the base of the cone having a larger diameter than the pulmonary vein. The base of the cone should have a diameter chosen in relation to the estimated predetermined size of the ostium so that it is about the same or slightly larger than the ostium, and prevents insertion of the base segment into the pulmonary vein. Pores 6 are located on the distal end of the balloon, on the distal tip of the conical segment of the balloon. This distal tip is of the conical segment of the balloon is sized to fit within the pulmonary vein, such that the fluid is only injected into the pulmonary vein when the balloon porous distal end is disposed within the pulmonary vein and fluid is provided to the balloon. The proximal portion of the balloon is watertight and non-porous, so that it does not permit fluid to exit the balloon near the base of the conical portion of the balloon. The fluid being injected interrupts electrical signals, and identification of a pulmonary vein which contains an arrythmogenic area is facilitated when the only electrical signals being interrupted are those of the pulmonary vein and not of the atrium itself. If the electrical signals of the atrium are inhibited then it is difficult to diagnose whether or not the atrial fibrillation has been prevented because the triggering signal from the pulmonary vein has been prevented or because the fluid has interrupted the atrial fibrillation in the atrium itself.

Figure 2:
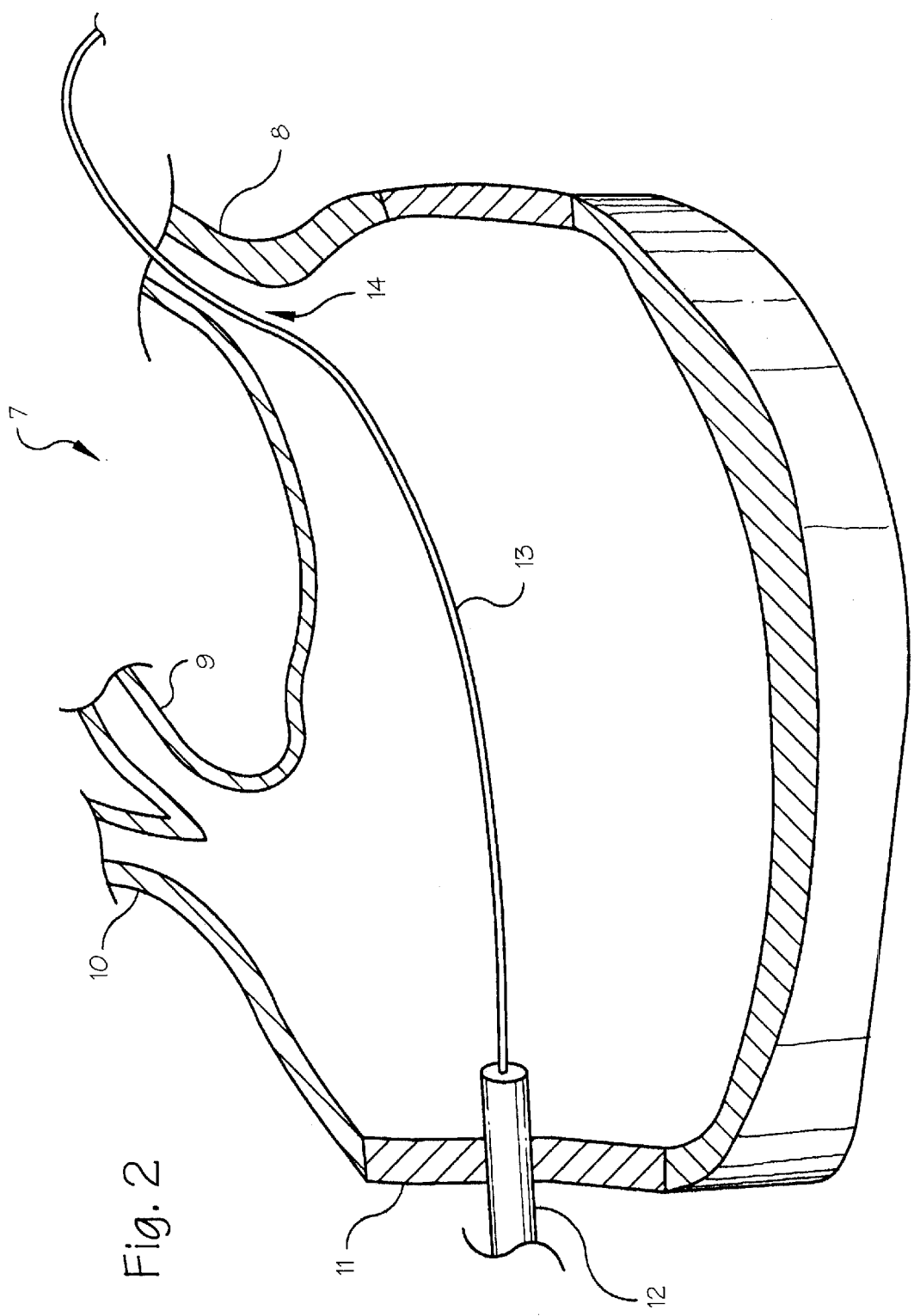
FIG. 2 is cross-sectional view of the left atrium with a guide wire entering the target pulmonary vein through a hole in the atrial septum.

FIG. 2 illustrates the method of accessing the pulmonary vein for placement of the diagnostic catheter. The left atrium 7 laid open to show the openings to the pulmonary veins 8, 9 and 10. The left atrium contains inlets of pulmonary veins which may be accessed from the right atrium (not shown) by passing a catheter 1 through the atrial septum 11 (with the catheter passing through an access hole cut into the atrial septum to allow passage of the catheter). To insert the diagnostic device into the pulmonary vein, access to the left atrium is first gained by percutaneous insertion of a catheter into the left atrium. To accomplish this, a needle catheter is placed through the venous system into the right atrium, and then penetrates the fossa ovalis (the atrial septum) to gain access to the left atrium. Access to the right atrium can be through the femoral vein in the thigh and the inferior vena cava, or may be through the subclavian vein, brachial vein or cephalic vein, etc., in the shoulder and arm, and then through the superior vena cava. A catheter sheath 12, such as a guiding catheter, is advanced over the needle catheter and is inserted into the left atrium. The needle catheter is then removed, and the diagnostic catheter is inserted. The distal end of the catheter is then maneuvered into the left atrium and into the target pulmonary vein. Once the catheter is passed through the access hole, then a guide wire 13 is inserted to locate the target pulmonary vein 8.

Figure 3:
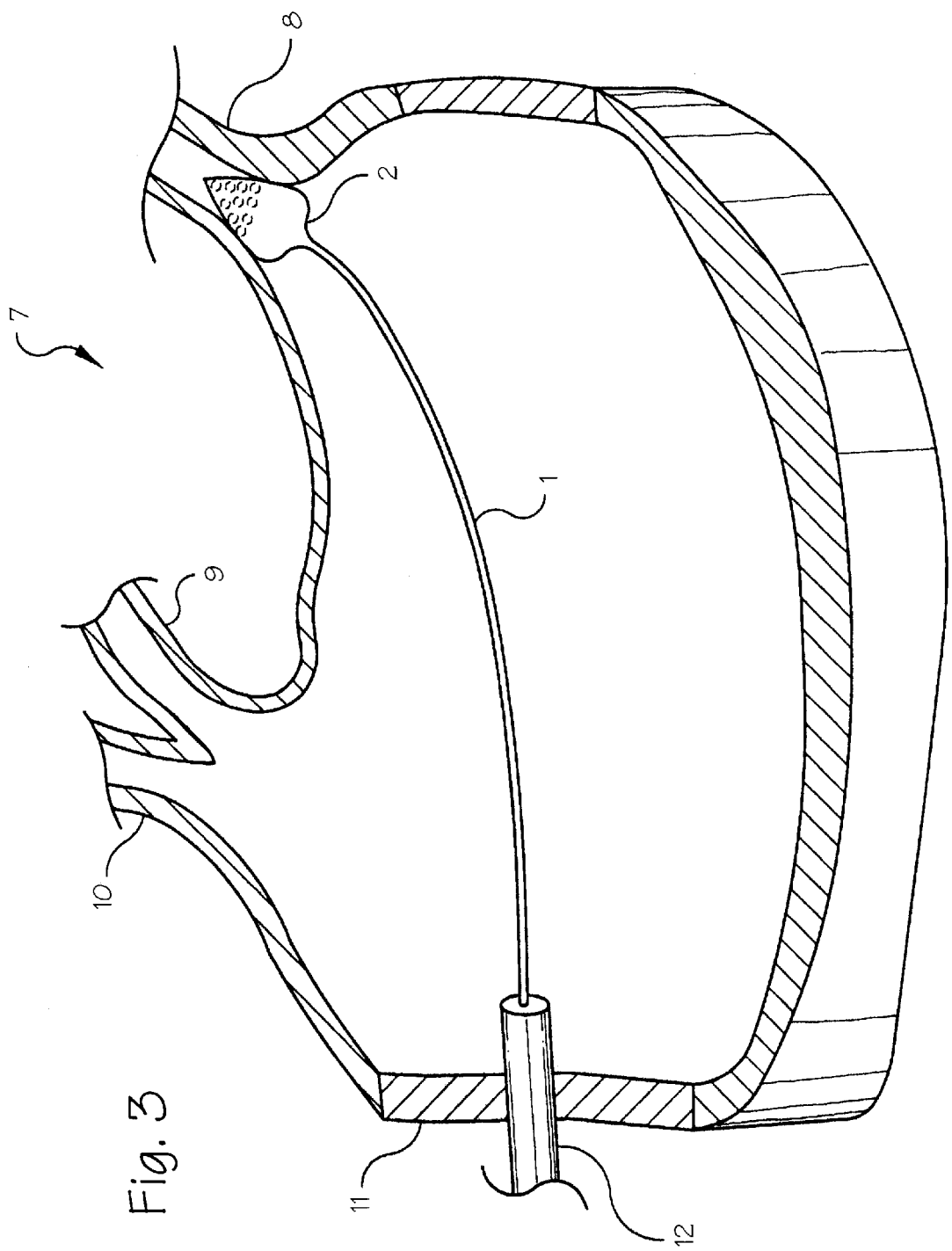
FIG. 3 illustrates the diagnostic balloon inserted into the target pulmonary vein where the balloon is in the expanded state thereby in contact with the ostium of the target pulmonary vein.

After the target pulmonary vein is located the diagnostic catheter is inserted into the target pulmonary vein, as in FIG. 3. Once the balloon 2 is placed within the ostium 14 of the target pulmonary vein it is expanded to contact the pulmonary vein walls. Location of the diagnostic balloon is confirmed and the balloon is expanded to the point where it engages the wall of the pulmonary vein. Preferably, the distal tip of the conical segment of the balloon will be disposed within the pulmonary vein, as shown, and the base of the conical segment will be located in the ostium and, when urged distally, will seat itself within the ostium. Once the balloon engages the wall of the target pulmonary vein, the fluid is administered to the target pulmonary vein. After the fluid has been administered it can be determined whether or not treatment of the pulmonary vein is necessary.

The method for diagnosing whether treatment of a target pulmonary vein will prevent atrial fibrillation in a patient includes several steps. The first step includes monitoring the patient's EKG to identify an atrial fibrillation. If atrial fibrillation is not occurring, then the physician performing the diagnosis may induce an atrial fibrillation. The second step includes inserting a diagnostic catheter into the heart and then into the target pulmonary vein, as described above. The third step includes injecting a diagnostic fluid into the target pulmonary vein through the pores of the balloon located at the distal end of the catheter. The diagnostic fluid is a fluid which disrupts electrical impulses of heart tissue, and preferably has a very short-lived effect, so the any disruption in naturally occurring arrythmia dissipates within an intra-operative time frame (several second to several minutes) and allows the physician to test another site. The last step includes determining whether the target pulmonary vein is where the atrial fibrillation is triggered. This is accomplished by monitoring the EKG of the patient and evaluating whether atrial fibrillation resolves after injection of the fluid.

After one or more catheters have been swapped out through the catheter sheath, the catheter sheath is removed, and the patient is closed. In most cases the opening through the fossa ovalis is very small and it heals up on its own. However, it is conceivable that a repair may be required in some patients using catheter techniques developed for closing septal defects.

The primary advantage of this device and method is that no tissue is unnecessarily damaged because the purpose of the diagnostic catheter is to diagnose the efficacy of a proposed pulmonary vein treatment prior to performing it. Such proposed pulmonary vein treatments could include ablation or stenting procedures.

A number of fluids may be used a diagnostic fluids in this method. Many pharmacologic agents prevent or slow conduction and can be used as the fluid which is administered to the target pulmonary vein. Cold saline or water may be used, since rapid cooling of electrically active heart tissue stops conduction of the tissue. Antiarrhythmic agents can also be used. It is preferred that the antiarrhythmic agent have a short pharmacodynamic half-life. Drugs that predominantly affect slow pathway conduction include digitalis, calcium channel blockers, and beta-blockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propafenone). The class III antiarrhythmic agents (sotolol or amiodorone) prolong refractoriness and delay or block conduction over fast or slow pathways as well as in accessory AV connections. Temporary blockade of slow pathway conduction is usually achieved by intravenous administration of adenosine or verapamil. [Scheinman, Melvin: Supraventricular Tachycardia: Drug Therapy Versus Catheter Ablation, Clinical Cardiology Vol. 17, Supp. II -11-II-15 (1994)]. Other agents such as encainide, diltiazem, and nickel chloride are also available.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A method for diagnosing whether ablation of a target pulmonary vein will prevent atrial fibrillation in a patient, said method comprising the steps of:
   monitoring an EKG of the patient to detect an atrial fibrillation;
   injecting a fluid for disrupting a potential electrical activity of the target pulmonary vein into the target pulmonary vein; and
   determining whether the target pulmonary vein is where the atrial fibrillation is triggered by again monitoring the EKG of the patient.

2. The method of claim 1, wherein the fluid is cooled saline.

3. The method of claim 1, wherein the fluid is an antiarrhythmic agent.

4. The method of claim 3, wherein the antiarrhythmic agent has a short pharmacodynamic half-life.

5. The method of claim 1 further comprising the step of inducing an atrial fibrillation if none is detected prior to injection of the fluid into the pulmonary vein.

6. A method for diagnosing whether ablation of a target pulmonary vein will prevent atrial fibrillation in a patient; said method comprising the steps of:
   monitoring an EKG of the patient;
   injecting a fluid through pores of a balloon into the target pulmonary vein; and
   determining whether the target pulmonary vein is where the atrial fibrillation is triggered by again monitoring the EKG of the patient.

7. The method of claim 6, further comprising the step of inducing an atrial fibrillation.

8. A method for diagnosing whether ablation of a target pulmonary vein will prevent atrial fibrillation in a patient, said method comprising the steps of:
   monitoring an EKG of the patient;
   inserting a catheter having a distal end into the target pulmonary vein, said catheter having a balloon located at the distal end of the catheter, the balloon having pores;
   injecting a fluid for disrupting the electrical impulse of the target pulmonary vein through the pores of the balloon into the target pulmonary vein; and
   determining whether the target pulmonary vein is where the atrial fibrillation is triggered by again monitoring the EKG of the patient to evaluate whether an atrial fibrillation is occurring.

9. The method of claim 8, further comprising the step of inducing an atrial fibrillation.

10. A method for diagnosing whether ablation of a target pulmonary vein will prevent atrial fibrillation in a patient; said method comprising the steps of:
    monitoring an EKG of the patient;
    inserting a catheter having a distal end into the target pulmonary vein, said catheter having a balloon located at the distal end of the catheter, the balloon having pores;
    injecting cooled saline through the pores of the balloon into the target pulmonary vein; and
    determining whether the target pulmonary vein is where the atrial fibrillation is triggered by again monitoring the EKG of the patient to evaluate whether an atrial fibrillation is occurring.

11. The method of claim 10, further comprising the step of inducing an atrial fibrillation.

* * * * *